(12) United States Patent
Lehmann

(10) Patent No.: US 8,336,397 B2
(45) Date of Patent: Dec. 25, 2012

(54) METHOD FOR MANUFACTURING OR TESTING METERED-DOSE-EJECTION DEVICES AND TESTING APPARATUS THEREFORE

(76) Inventor: Martin Lehmann, Wohlen (CH)

( * ) Notice: Subject to any disclaimer, the term of this patent is extended or adjusted under 35 U.S.C. 154(b) by 0 days.

(21) Appl. No.: 12/521,213

(22) PCT Filed: Apr. 29, 2009

(86) PCT No.: PCT/EP2009/055206
§ 371 (c)(1),
(2), (4) Date: Oct. 16, 2009

(87) PCT Pub. No.: WO2010/124732
PCT Pub. Date: Nov. 4, 2010

(65) Prior Publication Data
US 2012/0036943 A1  Feb. 16, 2012

(51) Int. Cl.
  *G01F 1/34* (2006.01)
(52) U.S. Cl. .................................. 73/861.42
(58) Field of Classification Search ............. 73/861.42
See application file for complete search history.

(56) References Cited

FOREIGN PATENT DOCUMENTS

| WO | WO 02/100469 A2 | 12/2002 |
| WO | WO 03/055539 A2 | 7/2003 |
| WO | WO 2007/112271 A2 | 10/2007 |

OTHER PUBLICATIONS

International Search Report and Written Opinion; International Application No. PCT/EP2009/055206; International Filing Date: Apr. 29, 2009.

*Primary Examiner* — Lisa Caputo
*Assistant Examiner* — Jamel Williams
(74) *Attorney, Agent, or Firm* — Antonelli, Terry, Stout & Kraus, LLP.

(57) ABSTRACT

For testing metered-dose-ejection devices, whether the ejected dose accords with a rated dose, the device (1) is sealingly applied (26) to a test compartment (24) and upon machine manipulation on the device (M, 5) a dose is ejected into the test compartment (24). Pressure difference established by such injection and with respect to a pre-established reference pressure (30) in the test compartment (24) is monitored by a pressure sensor (32). The output signal (o) of this sensor (32) is indicative of the extent of the addressed dose.

17 Claims, 3 Drawing Sheets

METHOD FOR MANUFACTURING OR TESTING METERED-DOSE-EJECTION DEVICES AND TESTING APPARATUS THEREFORE

RELATED APPLICATION

This application is a U.S. national phase application under 35 U.S.C. §371 of International Application No. PCT/EP2009/055206 filed Apr. 29, 2009.

DEFINITIONS

We understand under a "metered-dose-ejection" (MDE) device a device with a receptacle which contains a liquid or powderous product. Such device further comprises a manually operable manipulator. By each action upon the manipulator—customarily an actuating stroke—there is ejected from the outlet opening of the receptacle a dose of fluidic material. The receptacle may contain a propellant gas, customarily in liquid form, so that upon each stroke on the manipulator the dose of the addressed fluid is ejected through the receptacle outlet, driven by the propellant gas and thus as a dose of gaseous fluid. In other techniques pressure necessary to eject the addressed dose of gaseous fluid is built up only by actuation of the manipulator e.g. in a fluidizing device applied to the MDE device.

Still in other embodiments of such MDE the fluid content in the receptacle is pressurized in the recipient but only ejected as a gaseous fluid-dose with the help of an additional nozzle of a fluidizing device applied in the MDE.

Irrespective of the technique which is applied at or to such an MDE to eject a product contained in the receptacle, common to all these devices is that by one actuation upon the manipulator one dose of product is ejected which dose contains a predetermined, rated amount of the MDE-content.

A more specific category out of MDE devices are the so-called "metered-dose inhalers", MDI. They do contain powderous or liquid product and a propellant gas. The ejection opening comprises a projecting, tubular stub. This stub acts as the manipulator addressed above in that moving the stub coaxially into and towards the interior of the receptacle provides for ejecting a product dose out of the tubular stub. Such MDIs are widely known for medical appliances as for anti-allergic products to be inhaled.

We further understand under the generic term of a fluid:
  a gas
  a liquid
  a powder
  a gas containing liquid and/or powder We further understand under a gaseous fluid:
  a gas
  a gas containing powder and/or liquid Thus, in any case an MDI finally ejects a gaseous fluid, be it directly from the outlet of the receptacle or be it after respective treatment of a fluid from the receptacle within a fluidizer device.

Very often, the dose ejected by an MDE is critical with respect to its extent. This is especially and as an example the case for some medical products as from MDI devices to be applied in a well-controlled manner. MDE devices leaving manufacturing may be subject to relatively large tolerances with respect to a rated dose to be ejected or are even misassembled by combining a specific product contained in the receptacle with a wrong dosing manipulator or valve arrangement.

SUMMARY

It is an object of the present invention to provide MDE devices and thereby more specifically MDI devices the ejected dose of gaseous fluid being within predetermined limits equal to a rated dose.

This is achieved according to the present invention by a method of manufacturing metered-dose-ejection—MDE—devices with an affirmed rated ejection dose of gaseous fluid per ejecting manipulation. This method comprises:

sealingly connecting the ejection outlet of an unaffirmed MDE to a test compartment,
  machine performing an ejection manipulation upon the manipulator of the MDE, thereby ejecting a dose of gaseous fluid into the test compartment;
  monitoring pressure in the test compartment after having established a predetermined volume of the test compartment containing the ejected dose of gaseous fluid;
  exploiting the pressure monitored as an indication of whether the ejected dose accords, within predetermined limits, with a predetermined rated ejection dose or not
  and
  if it does, affirming to the MDE device to eject doses which accord to the predetermined rated dose.

Thus and according to this method an MDE which has been manufactured but which is not affirmed to eject doses of a fluid which accord to rated doses of gaseous fluid per ejecting manipulation are subjected to a further manufacturing step, according to a dose testing step, so that finally MDE devices result which eject doses of fluid according to a rated dose, i.e. which are only different from such rated dose within predetermined limits.

It is thus also within the frame of the present invention to propose a method for testing MDE devices to establish whether they do eject a predetermined rated dose of gaseous fluid per ejection manipulation upon the device or not. Thereby, as was addressed above, MDE devices are addressed which directly do eject respective doses of gaseous fluid or which eject a fluid which is only converted to a gaseous fluid with the help of a fluidizer device which is customarily removably applied to the receptacle. It is perfectly clear that in this latter case the method for manufacturing as addressed above as well as the method for testing as here addressed comprise the application of a respective fluidizer device to the MDE device. The method for testing as addressed comprises sealingly connecting the outlet of the MDE device to a test compartment;
  machine performing an ejection manipulation upon the MDE device, thereby ejecting a dose of gaseous fluid into the test compartment;
  monitoring pressure in the test compartment after having established a predetermined volume of the test compartment;
  exploiting the pressure monitored as an indication of whether the ejected dose accords, within predetermined limits, with the predetermined rated ejection dose or not.

In one embodiment of either methods, namely the method for manufacturing and the method for testing as addressed above, the test compartment comprises a piston/cylinder arrangement and further comprises machine performing the ejection manipulation by means of a movement of the piston relative to the cylinder of the piston/cylinder arrangement, departing from a predetermined relative position of the piston and cylinder and monitoring the pressure after return of the piston and cylinder in the predetermined relative position.

Thereby, this embodiment is especially suited for manufacturing or testing MDI devices whereat the ejection manipulation is performed by pushing a tubular outlet stub into the receptacle of the MDI device. By the fact that pressure monitoring is only established after the piston and cylinder have returned in their predetermined relative position it is made sure that such monitoring is always performed in a volume of predetermined, reference extent which is established by the addressed piston/cylinder arrangement when piston and cylinder are positioned in the addressed predetermined relative position.

In a further embodiment of the method as addressed above, which may be combined with all of the embodiments addressed to now as well as with those which will be addressed subsequently, there is machine performed at least one flushing manipulation, thereby generating respectively at least one flushing dose ejection before machine performing the one manipulation for ejecting that dose which is checked by pressure monitoring. Thereby, there is prevented that the at least one flushing dose does influence the pressure as monitored.

Thereby, one or more than one flushing doses are ejected from the MDE device before causing that dose to be ejected which is to be checked. Clearly in a most simple way the flushing doses are ejected into the test compartment too. Nevertheless, to prevent any influence of the pre-ejected flushing doses upon the measuring result, reference pressure is re-established in the test compartment after flushing. Reference pressure is customarily ambient pressure. In other words and making use of ambient pressure as reference pressure for pressure monitoring, after each or after a predetermined number of flushing dose ejection or even permanently during such flushing, the test compartment is open to ambient and if necessary pumped, before the test compartment is sealingly closed at reference pressure, establishing start condition for checking the respective MDE device.

In a further embodiment of the manufacturing and testing methods according to the invention, which further may be combined with any of the embodiments addressed to now and as will be addressed subsequently, the MDE device to be tested is machine-shaken before performing machine manipulation to eject the dose to be tested, thereby also preferable before performing flushing.

The shaking operation, which may be performed by all-around rotating the respective device or by oscillatingly swivelling the device about a predetermined swivelling angle, or which may be performed by linear shaking or in combination, the content of the MDE device is brought to the state as it has to be customarily brought for practical use.

Still in a further embodiment of the manufacturing as well as of the testing method according to the invention and which further may be combined with any of the already addressed as well as with any of the subsequently addressed embodiments, at least the dose ejected upon the one machine manipulation is subjected to filtering downstream the outlet of the MDE device. Clearly and if, as addressed above, flushing doses are ejected into the test compartment such filtering is also performed with respect to the addressed flushing doses. Thereby, it is prevented that ejected droplets or powder particles of the gaseous fluid accumulate to the inner surfaces of the test compartment, to the sensing surface of a pressure sensor, are penetrating into a pump etc., so that by such filtering the time period or operating cycles of the respective testing arrangement up to cleaning are significantly enlarged. Thereby, the addressed filtering is performed by a filtering member which is easily removed and replaced.

Still in a further embodiment of the manufacturing or the testing methods according to the present invention, which further may be combined with any of the already addressed embodiments as well as with the embodiments subsequently addressed, the method is performed upon a stream of subsequently conveyed MDE devices. Thus, the method according to the invention under all its aspects is perfectly suited for in-line testing and manufacturing MDE devices which are conveyed to a respective testing station or—machine with multiple testing stations in a stream and at high velocity.

Still in a further embodiment of the manufacturing as well as of the testing method according to the invention, which may be combined with all of the addressed embodiments, the MDE device is an MDI device.

The object upon which the present invention is based is further resolved by an apparatus for testing metered-dose-ejecting—MDE—devices, whether they do eject a predetermined rated ejection dose of gaseous fluid per ejection manipulation upon the device or not, within predetermined deviation limits with respect to the addressed rated ejection dose, which apparatus comprises:

a support for at least one MDE device;
a driven manipulator for causing the MDI device on the support to eject a dose of fluid from an ejection outlet;
a driven connector arrangement to be automatically sealingly applied to the ejection outlet and establishing flow communication of the ejection outlet to an inlet for gaseous fluid into a test compartment;
a pressure sensor with its sense input in flow communication with the interior of the test compartment.

In one embodiment of the addressed apparatus, which may be combined with all of the subsequently addressed embodiments, the apparatus is intended for testing MDE devices having a pressurized content and an outlet valve which is opened by moving a tubular, spring-biased outlet stub axially towards the interior of the receptacle of the device. According to this embodiment the support comprises a gripping member for gripping the MDE device and holding the device with the stub in a predetermined position. The test compartment comprises a piston/cylinder arrangement with a piston drivingly operable within the cylinder and coaxially to the stub in the addressed predetermined position. The cylinder has a front wall with a through-bore for the stub in the addressed predetermined position. There is further provided a drive arrangement which establishes a first relative movement of the gripping member and of the piston/cylinder arrangement so as to sealingly bias the device to the outer surface of the front wall and thereby forming the addressed driven connector arrangement while introducing the stub into the through-bore. The addressed drive arrangement further establishes for a movement of the piston, as the addressed driven manipulator, from a predetermined reference position within the cylinder towards the front wall and towards and onto the stub in the through-bore. Thereby, the stub is moved towards the interior of the device's receptacle. The addressed drive arrangement further establishes for a back movement of the piston in the cylinder, back into the predetermined reference position.

The cylinder and piston which form the test compartment define a first compartment volume in flow communication with the outlet stub, as the addressed stub is moved towards the interior of the recipient. They further define in the addressed predetermined position of the piston within the cylinder a second compartment volume in flow communication with the first cavity volume and with the sense input of the pressure sensor.

By this embodiment, in operation, the MDE device is gripped and sealingly biased towards the outer surface of the front wall of the piston/cylinder arrangement. Thereby, the tubular stub is passed through the through-bore in the addressed front wall. Thereafter, by relative movement of the piston within the cylinder, thereby still keeping sealing engagement of the device with the front wall of the piston/cylinder arrangement, the tubular stub of the device is pushed towards the interior of the device's receptacle, thereby causing a dose of fluid to be ejected into the addressed first volume of the test compartment. It is only after the piston and cylinder have re-assumed their predetermined relative position, thereby establishing for the second volume in flow communication with the first volume that a relevant pressure measurement is made. Thereby, the sum of first volume and second volume accord with a predetermined reference volume to establish dose-significant pressure measurement.

In one embodiment of the embodiment which was just addressed the piston has a further through-bore with an opening aligned with the through-bore of the front wall and abutting in a backspace cavity volume within the piston.

Thus, by means of the addressed backspace cavity in the piston there is established a cavity volume which is independent of the relative position of piston and cylinder. Because the piston is moved back into a predetermined reference position with respect to the cylinder, the variable volume established between the piston and the cylinder becomes in this predetermined relative position independent of the stroke performed by the piston within the cylinder. Thereby, for pressure monitoring in the addressed predetermined reference position an accurate constant reference volume is established.

In a further embodiment, which may be combined with any of the already addressed embodiments and embodiments still to be addressed, there is provided a filter member downstream the addressed connector in the test compartment.

With an eye on the embodiment with the backspace cavity volume in the piston and a through-bore aligned with the through-bore in the front wall and abutting in the addressed backspace cavity, it becomes evident that such filter element is preferably provided at the end of the through-bore in the piston abutting in the backspace cavity.

In a further embodiment of the just addressed embodiment the filter member is a replace part.

Still in a further embodiment of the apparatus according to the invention, which may be combined with all embodiments addressed to now as well as with the embodiments to be addressed, the support for the MDE device is drivingly shakeable.

Thereby, in one embodiment of realizing shakeability, the addressed support is drivingly swivellable about an axis, thereby preferably oscillatingly swivellable by a predetermined swivel angle.

In one embodiment the apparatus according to the invention and according to each and all embodiments as were addressed is tailored for testing MDI devices.

BRIEF DESCRIPTION OF DRAWINGS

The invention shall now be further described by means of examples and with the help of figures.

The figures show.

DETAILED DESCRIPTION

Figure 1:
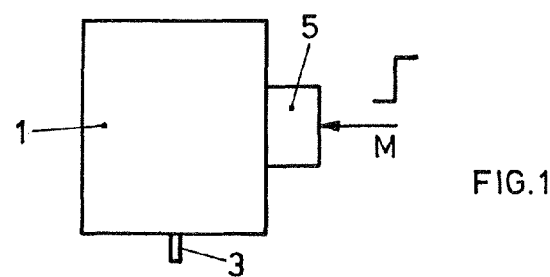
FIG. 1 most schematically, a generic metered-dose-ejection—MDE—device as addressed by the present invention.

FIG. 1 shows most generically and schematically an MDE device as addressed throughout the present description and claims. According to FIG. 1 an MDE device comprises a receptacle 1 with an outlet 3 and a manipulator 5. A one-stroke manipulation M exerted upon manipulator 5 results in a single dose D of fluid material ejected from outlet 3. Thus, irrespective of the time extent of the stroke manipulation M, a single dose D is ejected from outlet 3.

Figure 2:
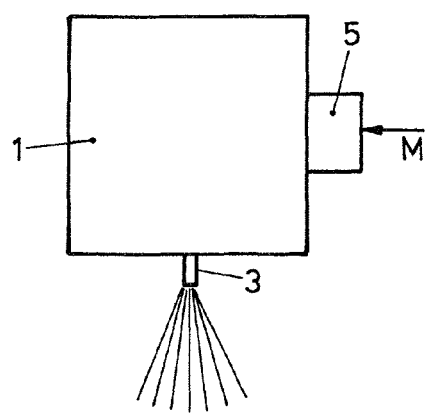
FIG. 2 in a schematic representation according to that of FIG. 1, one type of MDE device as of FIG. 1.

The addressed dose is thereby ejected by some types of MDE devices according to FIG. 2 directly as a gaseous fluid, as these types of MDE are pre-pressurized.

Figure 3:
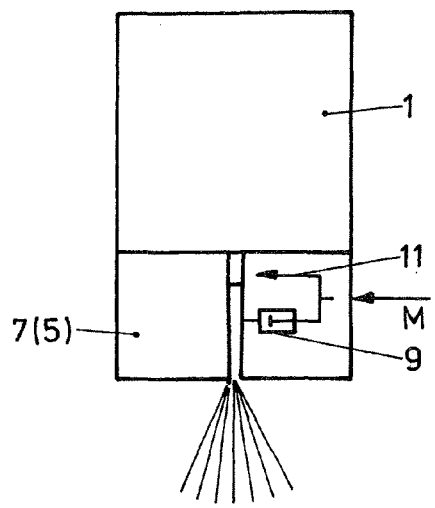
FIG. 3 in a schematic representation according to that of the FIG. 1 or 2, a second type of MDE device according to FIG. 1 and as addressed by the present invention.

At the second type of MDE devices as schematically shown in FIG. 3 the content of recectacle is liquid or powderous and not pressurized or not pressurized to an extent which would allow ejecting directly the content in gaseous fluidic form. For these types of MDE devices there is provided an externally mounted and often removable fluidizer device 7 which customarily simultaneously acts as manipulator 5. By this fluidizer device 7 and as schematically shown in FIG. 3 on one hand and upon a manipulation stroke M on a manipulator, the MDE device is caused to eject a dose of liquid or powderous material which is subjected to pressurizing due to the manipulation M in the fluidizer device 7 and is ejected as a gaseous fluid dose from fluidizer 7. We have schematically shown within the fluidizer 7 a pressurizing member 9 as well as an operational link 11 between that manipulation M and the MDE device to cause the latter to eject a dose of liquid or powderous material.

The FIGS. 1-3 show most generically types of MDE devices which are addressed by the present invention.

Figure 4:
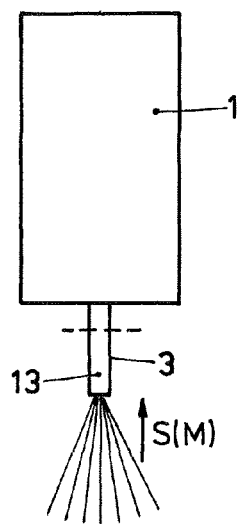
FIG. 4 in a schematic representation according to those of the FIGS. 1 to 3, an MDI device as a special type of an MDE device according to that of FIG. 2.

An MDI device, metered-dose-inflator, is a special type of MDE device and may be constructed according to the MDE type of FIG. 2 or the MDE type of FIG. 3. According to FIG. 4 an MDI device comprises a receptacle 1 having as an outlet 3 a tubular stub 13. This tubular stub 13 simultaneously operates as manipulator of the MDI device. By moving the tubular stub 13 which is spring-biased outwardly into the receptacle 1, the MDI device as represented in FIG. 4 ejects, as pre-pressurized, a dose of gaseous fluid. By each stroke S(M) upon the tubular stub 13 and irrespective how long the stub 13 is held in its inwards position (dashed line) there is ejected one dose of the content in gaseous fluidic form.

This type of MDI device thus accords with the more generic type of MDE device of FIG. 2.

Figure 5:
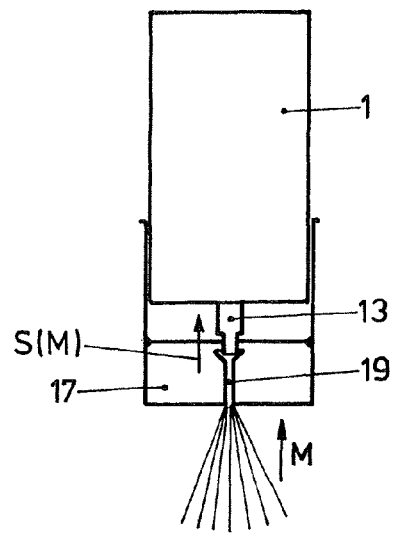
FIG. 5 an MDI device as a special type of an MDE device substantially according to the MDE device of FIG. 3 and in a schematic representation in analogy to those of the FIGS. 1-4 and as addressed by the present invention.

The type of MDI device according to FIG. 5 necessitates a fluidizer 17. Upon manipulation M the fluidizer 17 causes, as schematically shown in FIG. 5 by moving stub 13 according to arrow S(M) inwards, the MDI device to eject a dose of fluid content which is converted in gaseous fluidic form by a respective nozzle arrangement in the fluidizer 17, schematically shown at 19. As customarily MDI devices are pre-pressurized there is no need for pressurizing the respectively ejected fluidic dose by the ejection manipulation as in the more generic MDE embodiment of FIG. 3. Nevertheless, the MDI type as of FIG. 5 necessitates an additional nozzle arrangement for properly ejecting gaseous fluid as necessitated e.g. for inhalation purposes.

Figure 6:
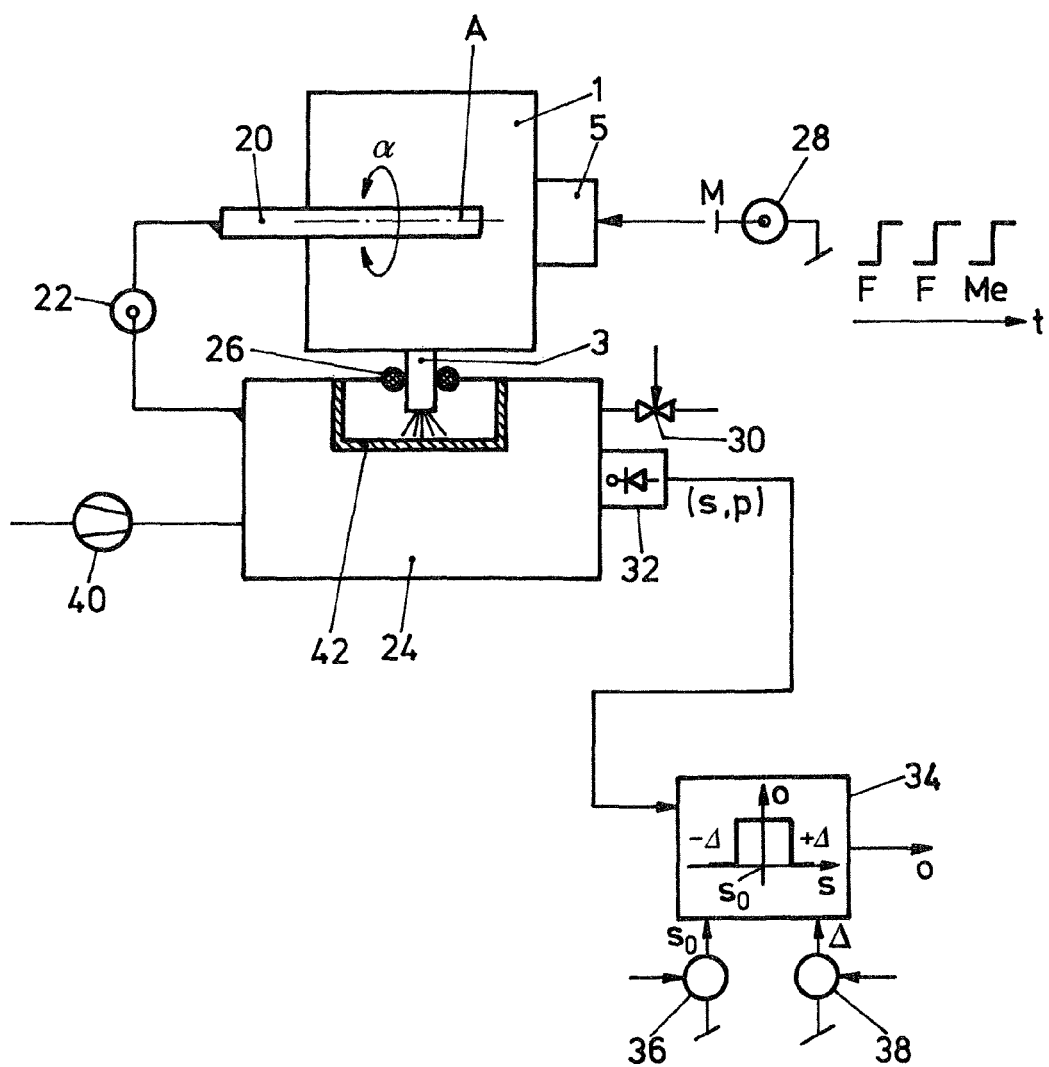
FIG. 6 by means of a simplified schematic functional-block/signal-flow representation, the principle of the methods according to the present invention and of an apparatus according to the invention, and FIG. 7 in a simplified cross-sectional representation, an embodiment of an apparatus according to the present invention and operating the methods according to the invention.

With the help of FIG. 6 the principle of the present invention shall be explained. Thereby, we base on the most generic MDE device type as was addressed in context with FIG. 1. The receptacle 1 of the MDE device is gripped by a gripping member 20 and held in a predetermined position. By means of a drive 22 the MDE device with outlet 3 is applied into flow communication with a test compartment 24, whereby automatically establishing sealing connection as schematically shown at 26 between the outlet 3 of the MDE device and the test compartment 24. By machine performing an ejection manipulation M, as schematically shown by a drive 28, a single dose of product is ejected from the MDE device into the test compartment 24. The test compartment 24 of predetermined reference volume is, before performing dose ejection, brought on a reference pressure as on ambient pressure as schematically shown via controlled valve 30. Clearly before ejecting the addressed dose into test compartment 24 valve 30 is closed. After ejection of the dose the resulting pressure in test compartment 24 is monitored by means of a pressure sensor 32, the sensing surface thereof being in communication with the interior of test compartment 24. Given the volume of the test compartment 24 being exactly known, the difference between reference pressure, customarily ambient pressure, and the resulting pressure after ejection of the dose of gaseous fluid into compartment 24 is an indication of the magnitude of the addressed dose. The electrical output signal s(p) of the pressure sensor 32 is applied to an evaluation unit 34, whereat it is compared with a signal range $s_o \pm \Delta$. The reference value $s_o$ according to a rated dose extent as well as the range $\pm \Delta$ are controllably input by respective sources 36 and 38 to the evaluation unit 34. Whenever the output signal S(p) of the pressure sensor 32 is within the range $S_o \pm \Delta$, the MDE device under test is considered to eject a dose which accords with a rated dose and an affirmative output signal o is generated by the evaluation unit 34. Thus, the respective MDE device under test is affirmed to eject the proper dose.

To increase significance of the measurement as performed according to the present invention it might be desirable to first eject from the MDE device under test one or more than one flushing doses before ejecting that dose which shall be subjected to pressure measurement. As schematically indicated in FIG. 6 there is thus applied one or more than one machine operated flushing manipulations F before the manipulation Me for ejecting the dose to be checked is performed. Thereby, it clearly would be possible to perform the flushing dose ejection before the MDE device is sealingly applied in flow communication with the test compartment 24. This would necessitate a separate removing system for the addressed flushing doses as customarily the content of the MDE device should not be freely ejected into ambient atmosphere. Thus, in the embodiment as schematically shown in FIG. 6, the flushing doses are also ejected into the test compartment 24. For removing these flushing doses from the test compartment 24 and establishing, before ejecting the dose to be checked, accurate starting conditions for pressure measurement, the test compartment 24 may then be emptied as by a pump 40 and opening valve 30. The outlet or inlet of pump 40 is applied to a respective filtering system for the material ejected from the MDE device. Further and in one embodiment, there is provided as schematically shown in FIG. 6, a filter member 42 just downstream the outlet 3 and within the test compartment 24. By this filter member 42 a significant part of liquid or powderous material which is ejected with the respective doses of gaseous fluid is collected, thereby preventing the walls of the test compartment 24 as well as a possibly provided pump 40, sensing surface of sensor 32, to be contaminated or too quickly contaminated, thereby significantly lengthening the time spans for cleaning maintenance of the test compartment 24. The filter element 42 is tailored and mounted as an easily replaceable part.

In a further generic embodiment it is taken into account that often an MDE device has to be shaken before a proper representative dose of product is ejected. In these cases the addressed requirement is considered by providing a shaking drive (not shown in FIG. 6) which shakes the MDE device before being sealingly applied in flow communication to the test compartment 24. Such shaking movement is thereby e.g. performed by a driven rotary oscillation as about an axis A according to FIG. 6 and by an oscillating angle α. Instead of oscillatingly swivelling the MDE device the addressed shaking may also be performed by linear oscillating or by rotation.

As has been addressed above, the generic principle of the present invention has been explained with the help of FIG. 6 based on a generic MDE device as shown in FIG. 1 and more specifically in FIG. 2. If an MDE type as was exemplified with the help of FIG. 3 is to be tested or is to be tested as one step of a manufacturing method, then the MDE is either applied together with the fluidizing device 7 and motor driven manipulation M is applied to such fluidizing member 7 according to FIG. 3. Alternatively, the test compartment is tailored to incorporate fluidizing member 7 so that the MDE devices to be tested may be applied to the test apparatus without each being provided with a fluidizing member 7. E.g. and with an eye on an MDI type as of FIG. 5, a fluidizing member 17 with fluidizing nozzle is then incorporated and part of the inlet to the test compartment 24.

Figure 7:
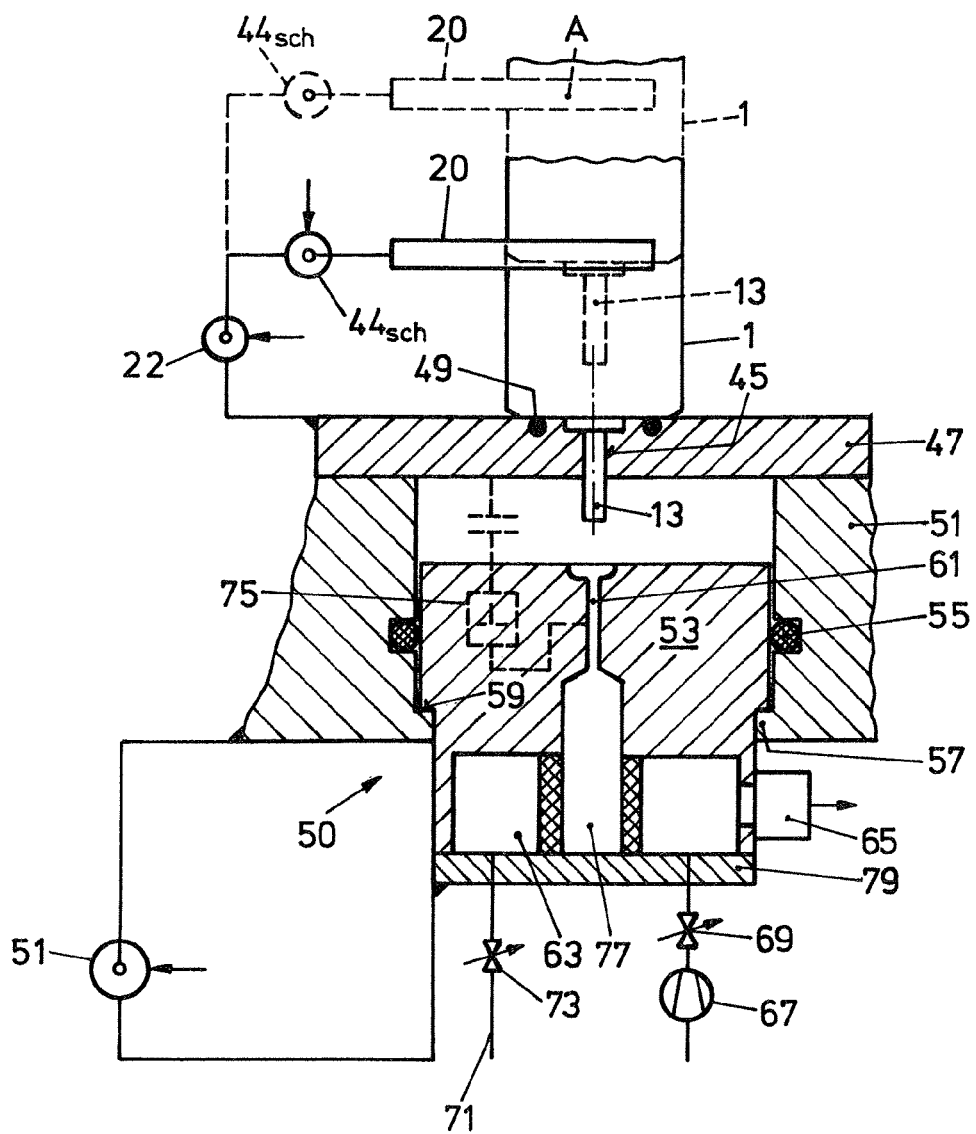

FIG. 7 shows in a sectional representation and simplified an apparatus according to the present invention and following the principle which has been exemplified with the help of FIG. 6. It is specifically tailored for MDI testing or manufacturing, primarily of that type as was described with the help of FIG. 4 or 5.

As shown in dashed lines, the receptacle 1 of an MDI device is first gripped by a support member 20 as of FIG. 6 and shaken oscillatingly about axis A. The drive for performing oscillating shaking is shown schematically at $44_{sch}$.

Thereafter, the MDI device with tubular outlet stub 13 is brought into a predetermined position wherein tubular stub 13 is coaxial with a receiving through-opening 45 in a front plate 47 of a piston/cylinder arrangement to be described.

By means of drive 22 according to FIG. 6, the MDI device after having been shaken and brought in predetermined position, is moved relative to plate 47 so as to introduce the tubular stub 13 into and through the through-bore 45 in the front plate 47. Sealing members as e.g. O-ring 49 coaxial to through-bore 45 at the front side of plate 47, make sure that when the MDI device is biased by drive 22 towards and onto plate 47, there is established an accurate seal.

The stub 13 projects as shown out of the trough-bore 45 towards the interior of the piston/cylinder arrangement generically denoted by 50. The piston/cylinder arrangement comprises a cylinder 51 which is closed by the front plate 47. Within the cylinder 51 there is drivingly propelled a piston 53, sealed with respect to the inner surface of cylinder 52 as schematically shown by seals 55 in a customary manner for sealing pneumatic pistons. The cylinder 51 comprises a rim portion 57 which forms a stop for a respective shoulder 59 of the piston, thereby establishing a predetermined lower reference position between cylinder 51 and piston 53. Coaxially to the through-bore 45 and thus to the tubular stub 13 of the MDI device introduced, the piston has a bore 61 open towards and aligned with through-bore 45 and abutting into a piston cavity 63. As further schematically shown in FIG. 7, pressure sensor 65 communicates with the piston cavity 63. Further, as schematically shown, a pump 67 communicates via a controllable valve 69 with the addressed volume 63 as well as a discharge line 71 via a controllable valve 73. The apparatus as shown in FIG. 7 and according to the invention operates the methods according to the invention as follows:

After the MDI device having been shaken and introduced into the through-bore 45 of front plate 47, the piston within cylinder 51 is risen by means of drive 51. Thereby, the end of tubular stub 13 comes in contact with the rim of bore 61 and is pushed upwards into the receptacle 1 of the MDI device. Thus, a dose of product is ejected from the MDI device through the inwards moved tubular stub 13, via bore 61 within piston 53 into the piston cavity 63. The piston 53 is retracted by drive 51 up to the stop 57/59 and the pressure in the piston cavity 63 is measured. Thereafter, line 71 is opened by opening valve 73 to discharge the overpressure in piston cavity 63 and to re-establish therein ambient pressure as a reference pressure for testing the next MDI device.

If one or more than one flushing doses shall be ejected before measurement, the piston 53 is risen and retracted one or more than one time to cause by respective action upon the tubular stub 13 the MDI device to eject one or more than one flushing doses into the piston cavity 63. Between each of the flushing dose-ejecting operations, line 71 is opened by means of controlled valve 73 and, after opening valve 69, the piston cavity is flushed. It is only after re-closing valve 73, stopping pump 67 and closing valve 69 that the piston 53 is risen, this time for causing a "testing" dose to be ejected which is monitored by sensor 65. The result of this monitoring is exploited as an indication whether the injected dose accords with a rated dose within limits e.g. as was addressed in context with FIG. 6.

If instead of an MDI according to the FIG. 4 type an MDI according to the FIG. 5 type is to be manufactured or tested, either such MDI device plus a fluidizing device 17 as of FIG. 5 is applied to the front plate 47 or bore 61 in the piston 53 is tailored as a nozzle to result in ejecting gaseous fluid into the piston cavity volume 63. If, still further and for some cases, the MDI device under test necessitates external pressurizing of the fluid product ejected from the tubular stub 13, a pressurizing cylinder arrangement as shown in dashed lines at 75 is installed within cylinder 53 so that by upwards movement of the cylinder 53 and via e.g. an additional pressurizing piston cylinder arrangement 75, the product ejected from the tubular stub 13 is additionally pressurized to result in a gaseous fluid ejected into the piston cavity 63. To prevent all the internal surfaces bordering the piston cavity 63 from being contaminated by an ejected product, a filter member 77 is provided just downstream the inlet opening of bore 61 into the cylinder cavity volume 63. The piston 63 is thereby assembled in a way to easily allow quick replacement of the filter member 77 e.g. by establishing a screw connection between a bottom plate 79 of the piston and the remainder part of piston 53.

Further, the overall arrangement which is shown in FIG. 7 with the MDI device in top-down position may be inverted to operate upon an MDI device in bottom-down position.

A multitude of testing apparatus or stations as most generically explained with the help of FIG. 6 or more specifically with the help of FIG. 7 may be arranged in-line on a machine, e.g. on the carousel of a machine and served by a stream of respective MDE devices to be tested on a feeding conveyor.

Finally, it must be emphasized that a device with a manipulator for continuously ejecting a fluid product may be operated as an MDE device by time controlling the duration of such manipulation. Clearly such devices operated as an MDE device are also addressed by the term "MDE" as of the present invention. In this case the rate of product output from such device per time unit is tested according to the invention, and the term "dose" is to be understood as "ejected material amount per time unit".

The invention claimed is:

1. A method of manufacturing metered-dose-ejection-MDE-devices with an affirmed rated ejection dose of fluid upon an ejecting manipulation comprising:
   sealingly connecting the ejection outlet of an unaffirmed MDE device to a test compartment;
   machine performing an ejection manipulation upon said MDE device, thereby ejecting a dose of said fluid as a gaseous fluid into said test compartment;
   monitoring pressure in said test compartment after having established a predetermined volume of said test compartment;
   exploiting said pressure monitored as indication of whether said ejected dose accords within predetermined limits with said predetermined rated ejection dose or not;
   if it does, affirming to said receptacle to eject doses according to said predetermined rated dose.

2. A method of testing metered-dose-ejection—MDE—devices whether they do eject a predetermined, rated ejection dose of fluid upon an ejection manipulation or not, comprising:
   sealingly connecting the outlet of an MDE device to a test compartment;
   machine performing a ejection manipulation upon said MDE device, thereby ejecting a dose of said fluid as a gaseous fluid into said test compartment;
   monitoring pressure in said test compartment after having established a predetermined volume of said test compartment;
   exploiting said pressure monitored as indication of whether said ejected dose accords within predetermined limits with said predetermined rated ejection dose or not.

3. The method of claim 1 or 2, said test compartment comprising a piston/cylinder arrangement and comprising machine performing said ejection manipulation by means of a movement of a piston relative to a cylinder of said piston/cylinder arrangement, departing from a predetermined relative position, and monitoring said pressure after return of said piston and cylinder in said predetermined relative position within a compartment of said piston/cylinder arrangement.

4. The method of one of claims 1 or 2, further comprising machine performing at least one flushing manipulation, thereby generating respectively at least one flushing dose ejection before machine performing said one manipulation and thereby preventing said at least one flushing dose to influence said pressure monitored.

5. The method of one of claims 1 or 2, further comprising machine shaking said MDE device before performing said one machine manipulation.

6. The method of one of claims 1 or 2, further comprising filtering doses ejected at an inlet for said ejected doses to said test compartment.

7. The method of one of claims 1 or 2 being performed upon a stream of subsequently conveyed MDE devices.

8. The method of one of claims 1 or 2, said MDE device being a metered-dose inhaler—MDI—device.

9. Apparatus for testing metered-dose-ejecting—MDE—devices whether they do eject a predetermined rated ejection dose of fluid upon an ejection manipulation or not, comprising:
a support for at least one MDE device;
a driven manipulator for causing said MDE device on said support to eject a dose of fluid from an ejection outlet;
a driven connector arrangement to be automatically and sealingly applied to said ejection outlet and establishing flow communication with a test compartment cavity;
a pressure sensor with its sense input in flow communication with said test compartment cavity.

10. The apparatus of claim 9 for testing MDE devices having an outlet valve being opened by moving a tubular spring-biased outlet stub axially towards the interior of said device,
said support comprising a gripping member for gripping the MDE device and holding said device with said stub in a predetermined position;
said test compartment comprising a piston/cylinder arrangement with a piston drivingly operable within a cylinder and coaxially to said stub in said predetermined position, said cylinder having a front wall with a through-bore for said stub in said predetermined position;
a drive arrangement establishing a first relative movement of said gripping member and said piston/cylinder arrangement so as to sealingly bias said device to the outer surface of said front wall while introducing said tubular stub into said through-bore and further to establish a second movement of said piston from a predetermined reference position within said cylinder in said cylinder towards said front wall and towards and onto said tubular stub in said through-bore so as to move said stub towards said interior of said receptacle and still further establishing a back movement of said piston in said cylinder back into said predetermined reference position;
said cylinder and piston defining in said predetermined reference position a test compartment cavity of predetermined volume being in flow communication with said sense input of said pressure sensor.

11. The apparatus of claim 10, said piston having a further through-bore with an opening aligned with said through-bore in said front wall and abutting in a backspace cavity in said piston.

12. The apparatus of one of claims 9 to 11, further comprising a filter member downstream said connector arrangement and upstream at least a part of said test compartment cavity.

13. The apparatus of claim 12, said filter member being a replace part mounted within said piston.

14. The apparatus of one of claims 9 to 11, said support being drivingly shakeable.

15. The apparatus of claim 14, said support being drivingly swivellable about an axis.

16. The apparatus of one of claims 9 to 11 for testing metered-dose-inhaler—MDI—devices.

17. A method according to one of claims 1 or 2 or an apparatus according to one of claims 9 to 11 wherein said MDE device is established by a device for continuous ejection of a product upon ongoing operation of a manipulator and by monitoring or predetermining a manipulation time span.

* * * * *